(12) United States Patent
Kleeman et al.

(10) Patent No.: US 6,723,043 B2
(45) Date of Patent: Apr. 20, 2004

(54) METHODS AND DEVICES FOR INSERTING AND MANIPULATING SURGICAL INSTRUMENTS

(75) Inventors: Thomas J. Kleeman, Bedford, NH (US); James P. Duncan, Southaven, MS (US)

(73) Assignee: SDGI Holdings, Inc., Wilmington, DE (US)

( * ) Notice: Subject to any disclaimer, the term of this patent is extended or adjusted under 35 U.S.C. 154(b) by 15 days.

(21) Appl. No.: 09/963,143

(22) Filed: Sep. 25, 2001

(65) Prior Publication Data

US 2003/0060687 A1 Mar. 27, 2003

(51) Int. Cl.$^7$ .............................. A61B 1/32; A61B 17/00
(52) U.S. Cl. ........................................... 600/201; 606/1
(58) Field of Search ................. 606/1, 61, 86, 606/91, 99, 104; 600/201

(56) References Cited

U.S. PATENT DOCUMENTS

| | | | |
|---|---|---|---|
| 5,352,219 A | | 10/1994 | Reddy ............................ 606/1 |
| 5,441,059 A | * | 8/1995 | Dannan ...................... 128/898 |
| 6,159,200 A | * | 12/2000 | Verdura et al. ................ 606/1 |
| 2002/0116006 A1 | * | 8/2002 | Cohen ......................... 606/99 |

FOREIGN PATENT DOCUMENTS

| | | |
|---|---|---|
| WO | WO 96/05773 | 2/1996 |
| WO | WO 99/52453 | 10/1999 |
| WO | WO 01/49188 | 7/2001 |

OTHER PUBLICATIONS

*Reduced Profile Instrumentation Surgical Technique*, as described by J. Kenneth Burkus and John D. Dorchak, M.D.; Sofamor Danek, ©1999.
*Anterior Instrumentation Surgical Technique*, as described by Scott H. Kitchel, M.D.; Sofamor Danek, ©1999.
*Surgical Technique Using Bone Dowel Instrumentation for Anterior Approach*, Sofamor Danek, The Spine Specialist, 1996.
*LT–Cage Lumbar Tapered Fusion Device Surgical Technique*, as described by Thomas A. Zdeblick M.D. and J. Kenneth Burkus, M.D., Medtronic Sofamor Danek ©2000.

* cited by examiner

Primary Examiner—Cary E. O'Connor
(74) Attorney, Agent, or Firm—Woodard, Emhardt, Moriarty, McNett & Henry LLP

(57) ABSTRACT

The present invention is directed to a surgical instrument assembly that includes an operative element and an insertion instrument removably engageable to the operative element. The insertion instrument is positionable in a patient with the operative element engaged thereto to position the operative element at an operative site in the patient. A transfer instrument is removably engageable to the operative element when the operative instrument is located at the operative site. The insertion instrument can then be removed. Methods for using the surgical instrument assembly are also disclosed.

60 Claims, 13 Drawing Sheets

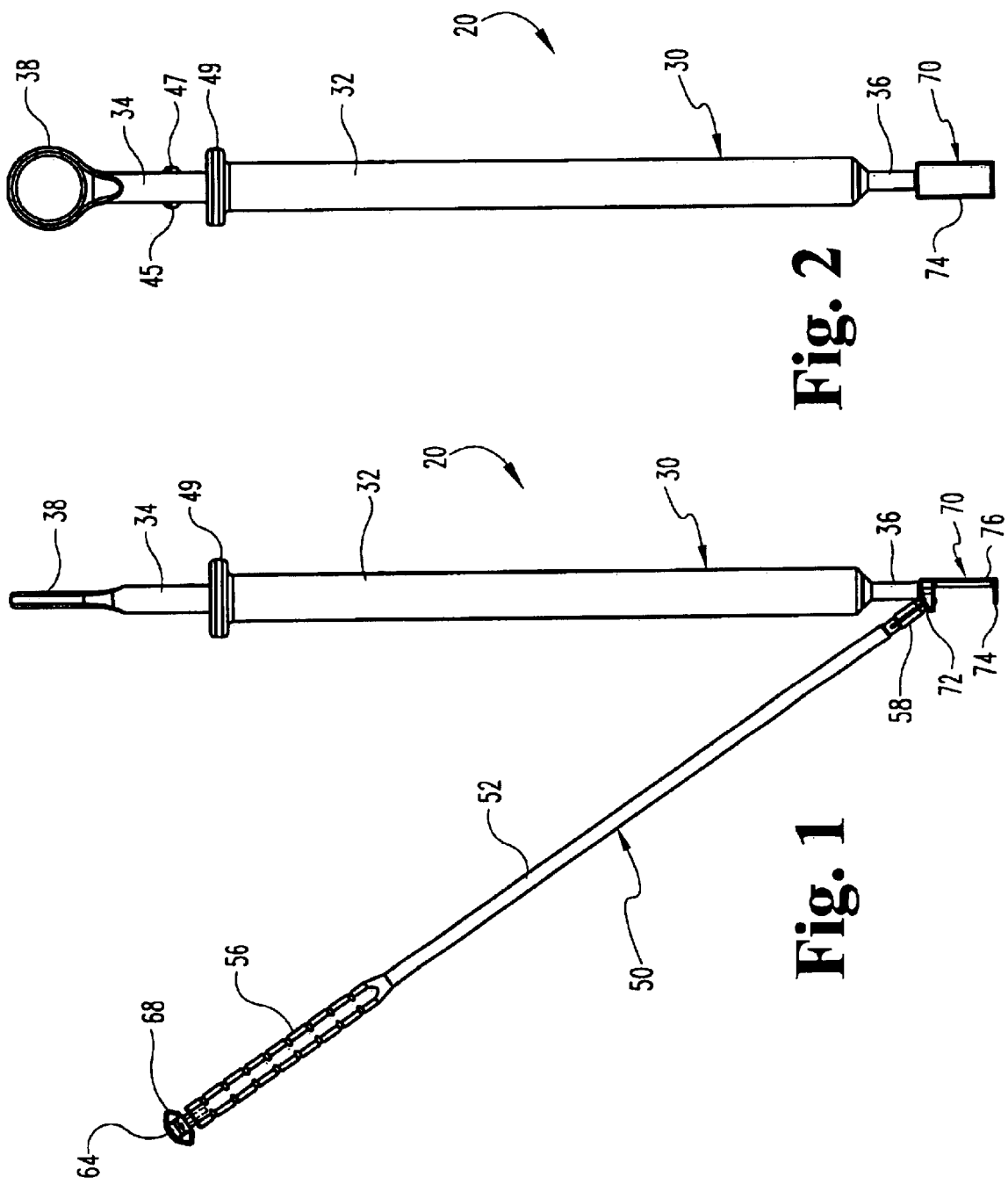

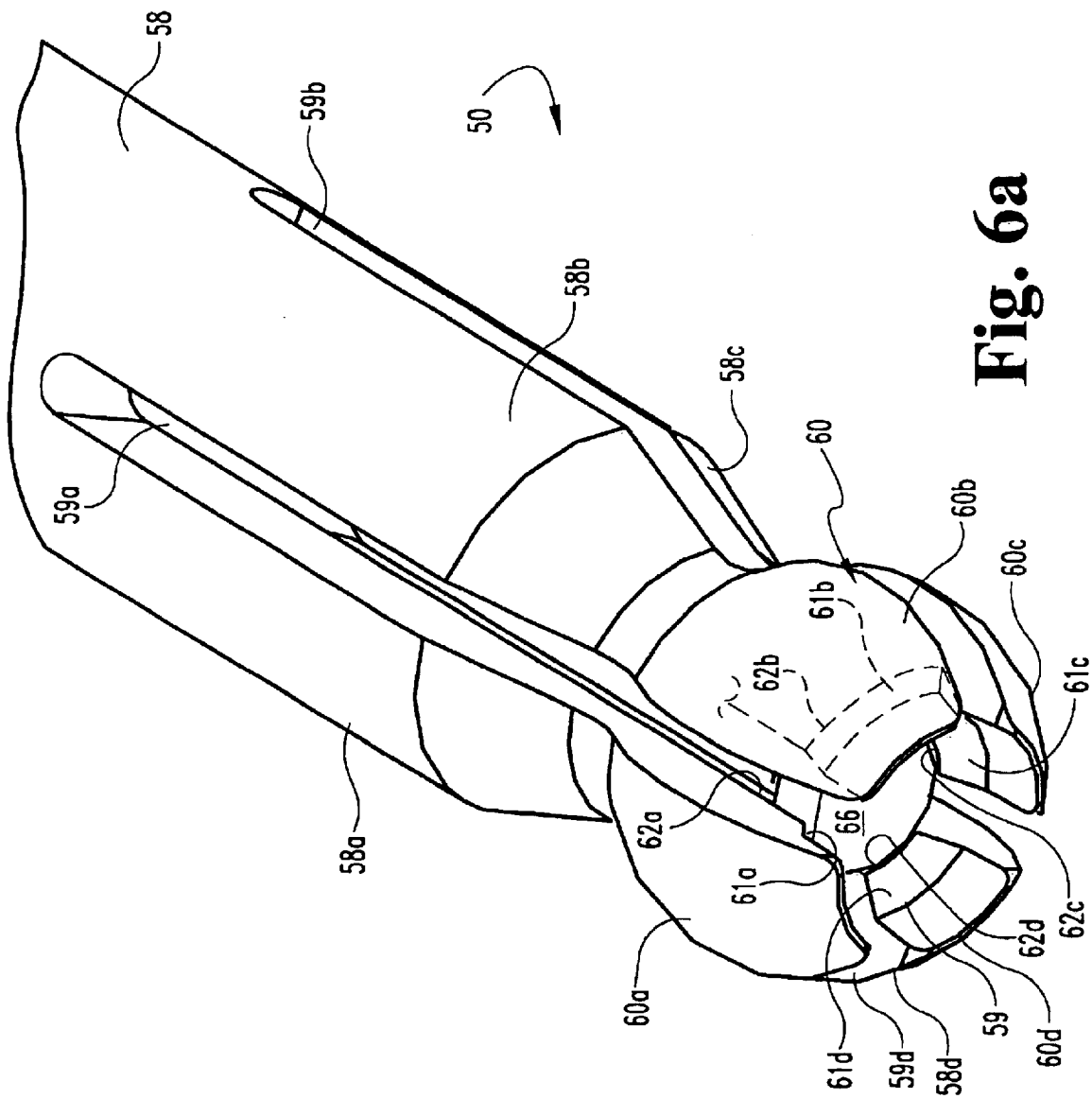

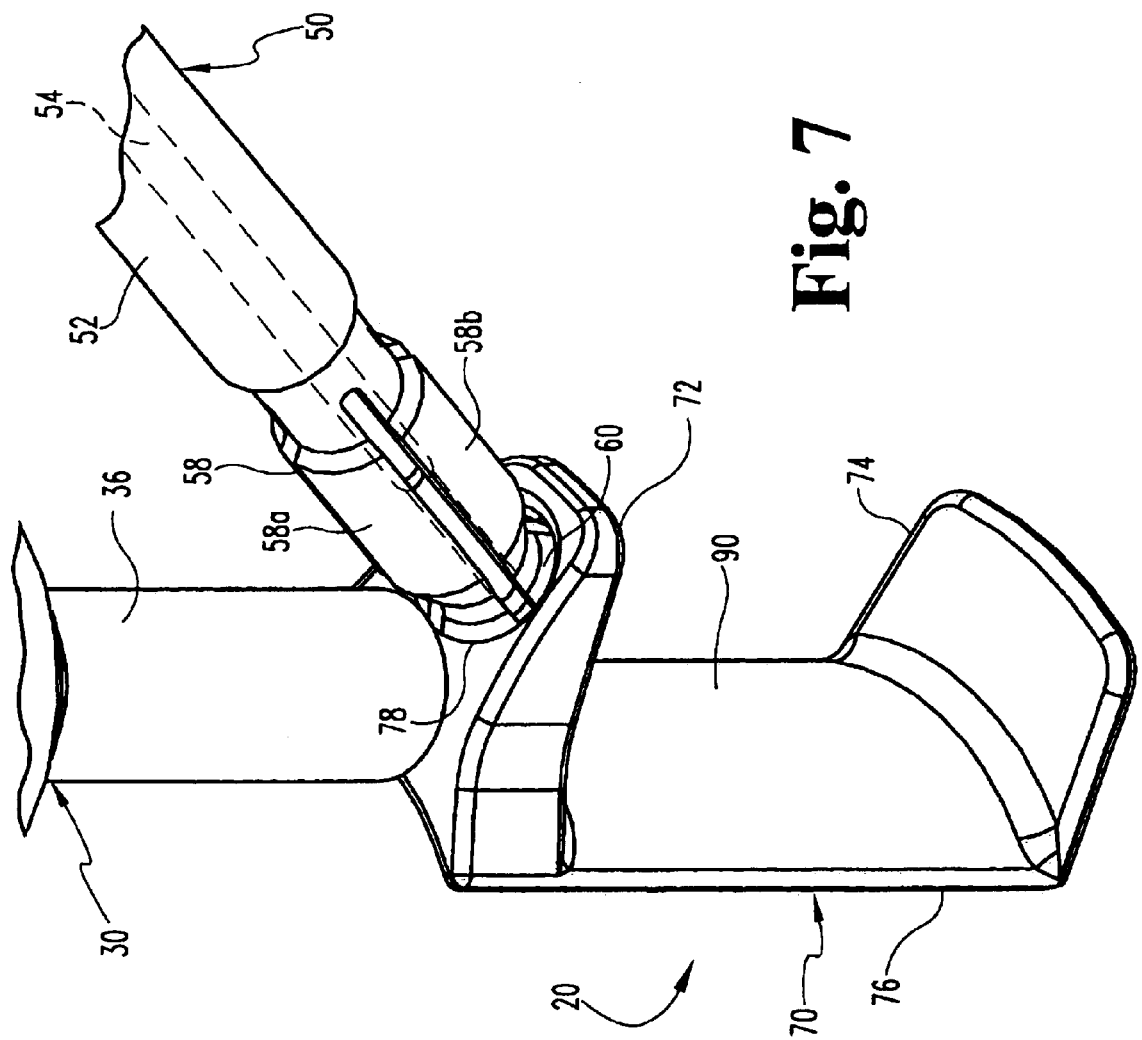

METHODS AND DEVICES FOR INSERTING AND MANIPULATING SURGICAL INSTRUMENTS

FIELD OF THE INVENTION

The present invention relates instruments and methods for inserting and manipulating surgical instruments.

BACKGROUND OF THE INVENTION

Various instruments and methods have been developed for surgical procedures that employ an anterior approach to an operative site in a patient through one or more access sleeves, through an open surgical procedure, or through one or more micro-incisions. Endoscopic visualization along with other known visualization instruments and insufflation techniques can be used during such procedures to aid in surgeon visualization and access of the operative site. Such procedures can be used to access the spinal column to perform surgical procedures including discectomies; disc space distraction and preparation; artificial disc, interbody spacer, or fusion implant insertion; and/or installation of plates, rods, cables, tethers along with the associated hardware for engaging the vertebral bodies. Locations other than the spinal column can also be accessed through an anterior approach to perform surgical procedures at an operative site in a patient.

One problem associated with anterior approaches to a surgical site is that the vasculature anatomy and other anatomic structures limit the working space available to the surgeon. Another problem is that operative instruments and elements inserted to the operative site occupy working space that could be better utilized by the surgeon if available to him or her. This limitation in the available working space makes some procedures difficult, impracticable, and/or unsafe for the surgeon to conduct. There remains a need for instruments and methods that can be employed in anterior approaches that provide the surgeon greater access to the operative site. The present invention is directed to meeting these needs, among others.

SUMMARY OF THE INVENTION

The present invention provides a surgical instrument assembly and method for an anterior surgical approach that provide the surgeon greater access to the operative site in a patient's body. In one form, the surgical instrument assembly includes an operative element coupled to an insertion instrument for inserting the operative element. A transfer instrument is then coupled to the inserted operative element. The insertion instrument is then removed and the transfer instrument maintains the operative element at the surgical site and can also be used to manipulate and reposition the operative element.

The surgical instrument assembly of the present invention can be inserted through access sleeves into the patient in an insufflated or non-insufflated environment, through micro-incisions, or through open surgical procedures in which the skin and tissue is retracted to expose the operative site.

In one specific application, the insertion instrument and operative element are inserted through a first port sized to receive the operative element. The transfer instrument is inserted through a second smaller port through which the operative is too large for insertion. The transfer instrument is coupled to the operative element, and the insertion instrument is removed from the first port. The first port is available to receive other surgical instruments for performing other procedures at the operative site.

In a further form, a vein retractor operative element is provided along with surgical techniques employing the same with the surgical instrument assembly of the present invention.

Other aspects, forms, embodiments, objects, features and advantages of the present invention will be apparent from the following description of the illustrated embodiment.

BRIEF DESCRIPTION OF THE FIGURES

FIG. 1 is a front elevational view of a surgical instrument assembly according to the present invention.

FIG. 2 is a side elevational view of the surgical instrument assembly of FIG. 1.

FIG. 6a is an enlarged perspective view of the distal end of the transfer instrument comprising a portion of the surgical instrument assembly of FIG. 1.

FIG. 7 is an enlarged perspective view illustrating the insertion instrument and the transfer instrument coupled to the operative element.

DESCRIPTION OF THE ILLUSTRATED EMBODIMENTS

Figure 3:
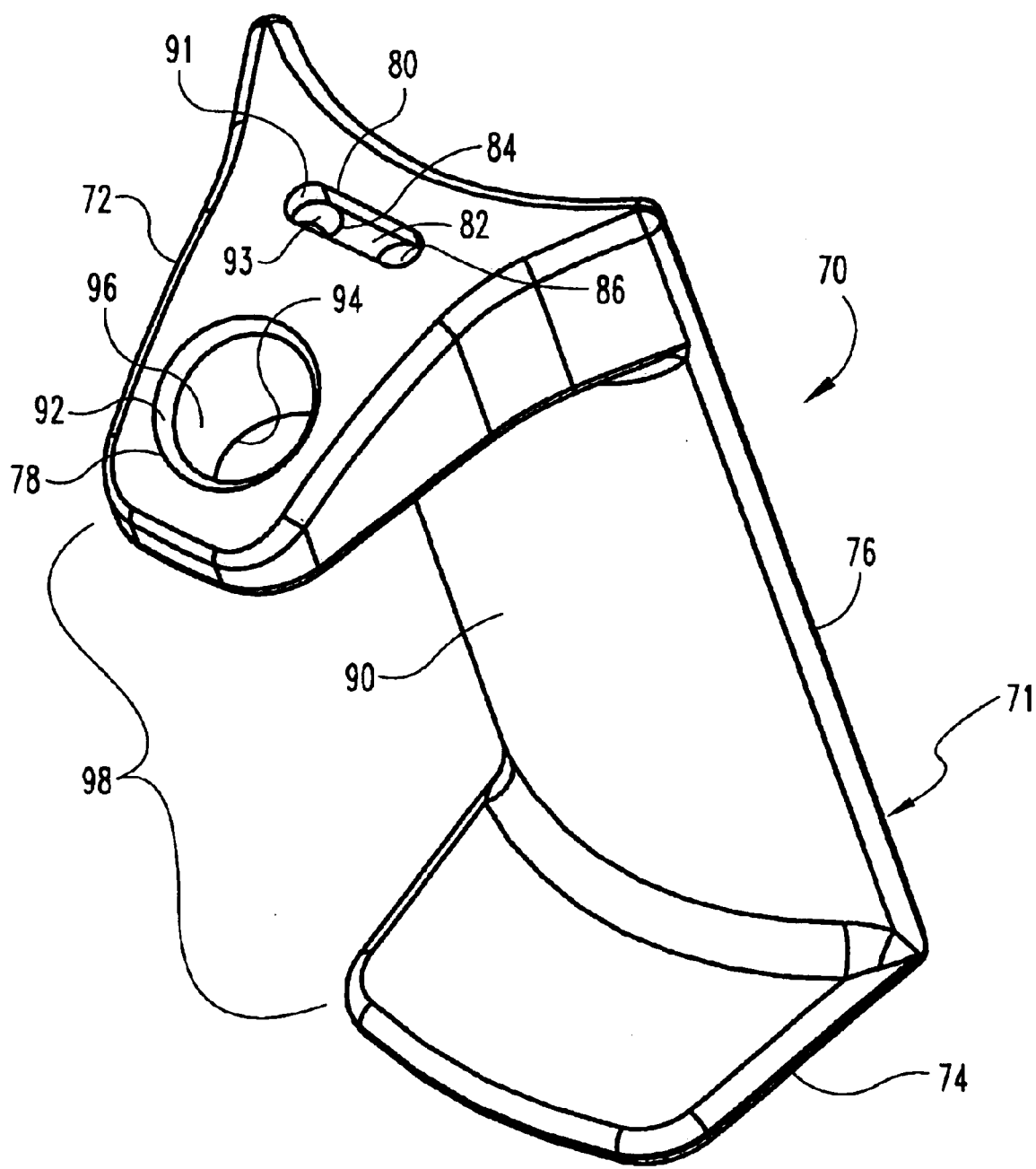
FIG. 3 is a perspective view of an operative element comprising a portion of the surgical instrument assembly of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device and any such further applications of the principles of the invention as illustrated therein are contemplated as would normally occur to one skilled in the art to which the invention relates.

Referring now to FIGS. 1 and 2, there is illustrated a surgical instrument assembly 20 for use surgery on a patient to position an operative element at an operative site in a patient. Surgical instrument assembly 20 has application in minimally invasive approaches in insufflated or non-insufflated working spaces, in open surgical procedures, in micro-surgeries and through access sleeves. In one specific application, surgical instrument assembly 20 is used in surgical procedures that require accessing the spine from an anterior approach. However, it should be understood that surgical instrument assembly 20 also has application in other types of surgeries and in other locations of the body such as would occur to those skilled in the art upon understanding of the present invention.

Surgical instrument assembly 20 includes an insertion instrument 30, a transfer instrument 50 and an operative element 70. It is contemplated in one form of the present invention that insertion instrument 30 is fixedly and removably coupled to operative element 70 and that transfer instrument 50 can be pivotally and removably coupled to operative element 70. Other forms of the present invention contemplate that insertion instrument 30 can be pivotally coupled to operative element 70 and/or transfer instrument 50 can be fixedly coupled to operative element 70.

In the illustrated embodiment, the operative element is a vein retractor that, as described in further detail below, is positionable in the body of the patient to retract vasculature and increase the surgeon's access to the operative site. Other embodiments contemplate that operative element 70 can have other forms, such as a distractor, blunt dissector, a light source, a tissue retractor, or cutting, reaming, and drilling instruments to name a few.

Figure 4:
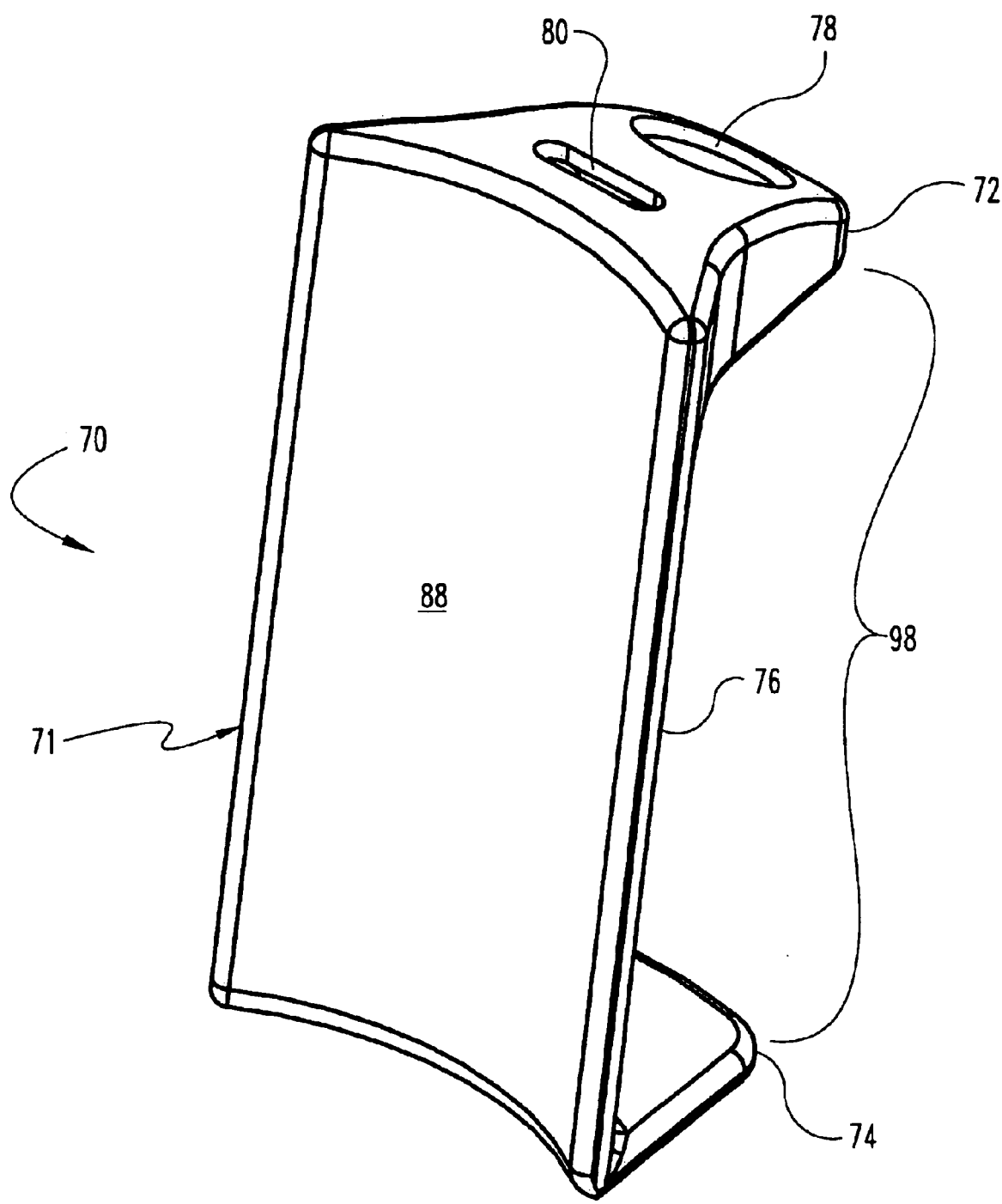
FIG. 4 is a perspective view of the operative element of FIG. 3 looking in the direction generally opposite that of FIG. 3.

Referring now further to FIGS. 3 and 4 of the illustrated embodiment, one specific form of operative element 70 is illustrated in the form of a vein retractor 71. Operative element 70 includes an upper first flange 72, a lower second flange 74 and a body 76 extending therebetween. First flange 72 and second flange 74 define a cavity 98 therebetween. Body 76 includes a concave surface 88 and an opposite convex surface 90 along cavity 98. Surfaces 88, 90 extend between first flange 72 and second flange 74. One or more arteries or veins can be placed and retracted away from the operative site to increase the surgeon's access thereto and also to protect the retracted vasculature.

First flange 72 includes a transfer instrument receptacle 78 and an insertion instrument receptacle 80 formed therein. Transfer instrument receptacle 78 can be provided with an upper lip 92 and a lower lip 94, and a concave surface 96 extending between upper lip 92 and lower lip 94 around receptacle 78. Concave surface 96 forms a partially spherical surface to which transfer instrument 50 can be removably and pivotally engaged, as describe further below.

Insertion instrument receptacle 80 includes a recess 82 formed in an upper surface of first flange 72. A first bore 84 is spaced from a second bore 86 and each extends into first flange 72 from recess 82. First bore 84 includes an upper lip 91 which is undercut by a concave, partially spherical surface 93 that extends along at least a lateral side thereof.

Second bore 86 is configured similarly to first bore 84 and includes a lip that is undercut by a partially spherical surface.

Figure 5:
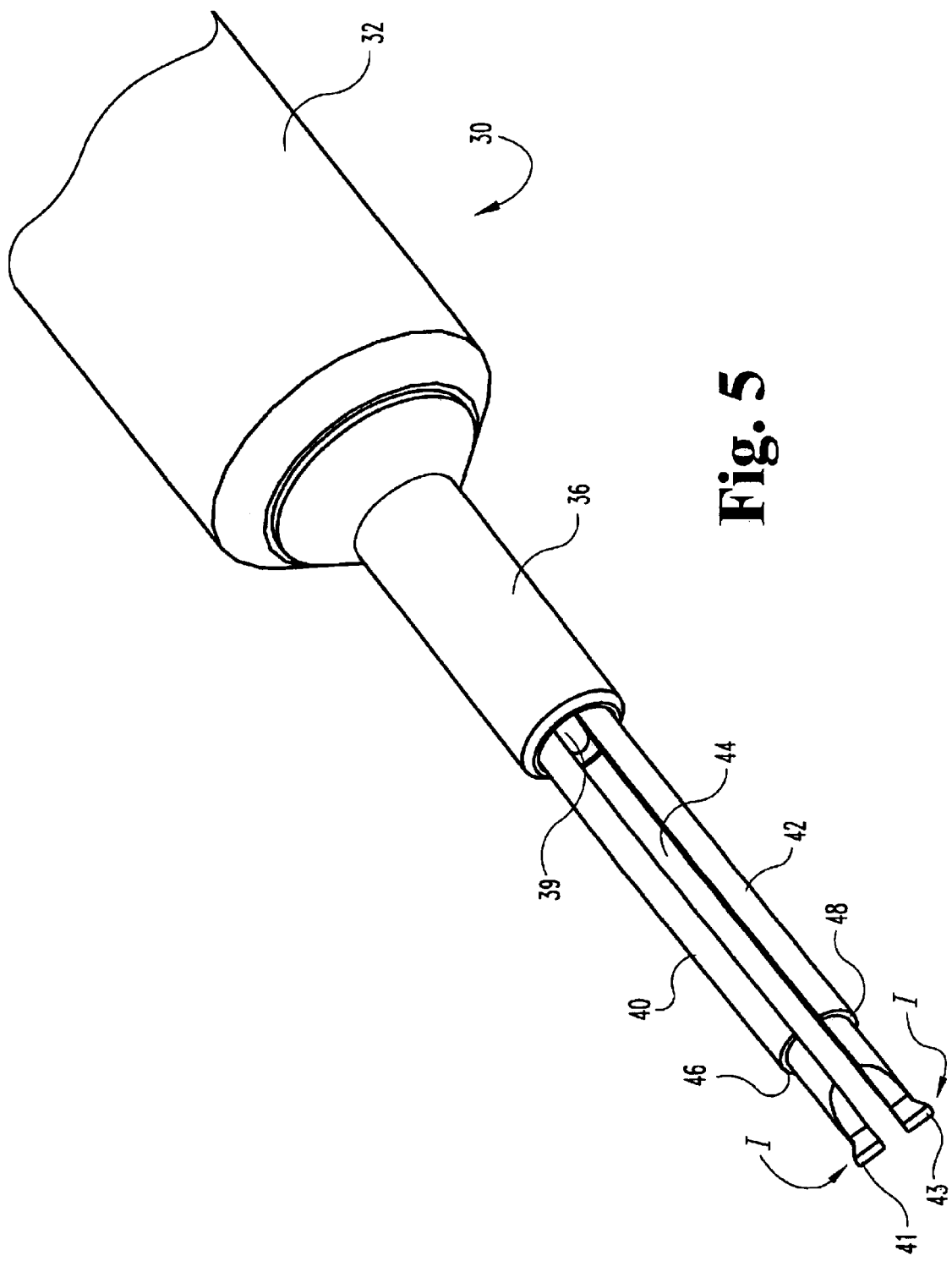
FIG. 5 is an enlarged perspective view of the distal end of the insertion instrument comprising a portion of the surgical instrument assembly of FIG. 1.

Referring now further to FIG. 5, insertion instrument 30 includes an outer sleeve 32 in which an inner shaft 34 is slidingly received. A finger flange 49 extends radially outwardly from the proximal end of outer sleeve 32. A locking member 36 is mounted to the distal end of outer sleeve 32. Locking member 36 defines a passage through which engaging members 40, 42 extend. Engaging members 40, 42 extend from a distal end of inner shaft 34, and have a slot 44 extending therebetween. Locking member 36 has a pin 39 at a distal end thereof engaged thereto and extending in the passage and positioned through slot 44 between engaging members 42, 44. Engaging members 42, 44 include stepped surfaces 46, 48 formed radially about engaging members 40, 42. Engaging members 40, 42 include radially outwardly extending projections 41, 43 that are engageable in first bore 84 and second bore 86 of insertion instrument receptacle 80.

A handle 38 extends from the proximal end of inner shaft 34. Handle 38 is illustrated in the form of a thumb ring; however, other handle types are contemplated such as a push button or the like. Insertion instrument 30 has an unlocked position in which inner shaft 34 is advanced distally with respect to outer sleeve 32 so that engaging members 40, 42 are substantially exposed as shown in FIG. 5. In this unlocked position, engaging members 40, 42 and projections 41, 43 are easily flexed toward another in the direction or arrows I for positioning projections 41, 43 past the upper lips and into the partially spherical portions of bores 84, 86, respectively.

Insertion instrument 30 is movable to a locked position, as shown in FIG. 7, by moving inner shaft 34 and outer sleeve 32 with respect to one another via handle 38 and finger flange 49, thereby advancing releasing member 36 toward projections 41, 43. In this locked position, pin 39 is also advanced distally in slot 44 and in contact with engaging members 40, 42, thus preventing projections 41, 43 from moving toward one another in the direction of arrows I. Since engaging members 40, 42 cannot flex, projections 41, 43 are fixed in the undercut portions of bores 84, 86 to couple operative element 70 to insertion instrument 30. In order to uncouple insertion instrument 30 from operative element 70, protuberances 45, 47 are aligned with slots (not shown) in finger flange 49 and outer sleeve 32 by rotating outer sleeve 32 about inner shaft 34 if necessary. Outer sleeve 32 can then be withdrawn proximally with respect to inner shaft 34 to the unlocked position so that projections 41, 43 are moveable toward one another and out of contact with the undercut portions of bores 84, 86 as insertion instrument 30 is withdrawn. Protuberances 45, 47 assist in preventing accidental uncoupling of insertion instrument 30 from operative element 70.

Figure 6B:
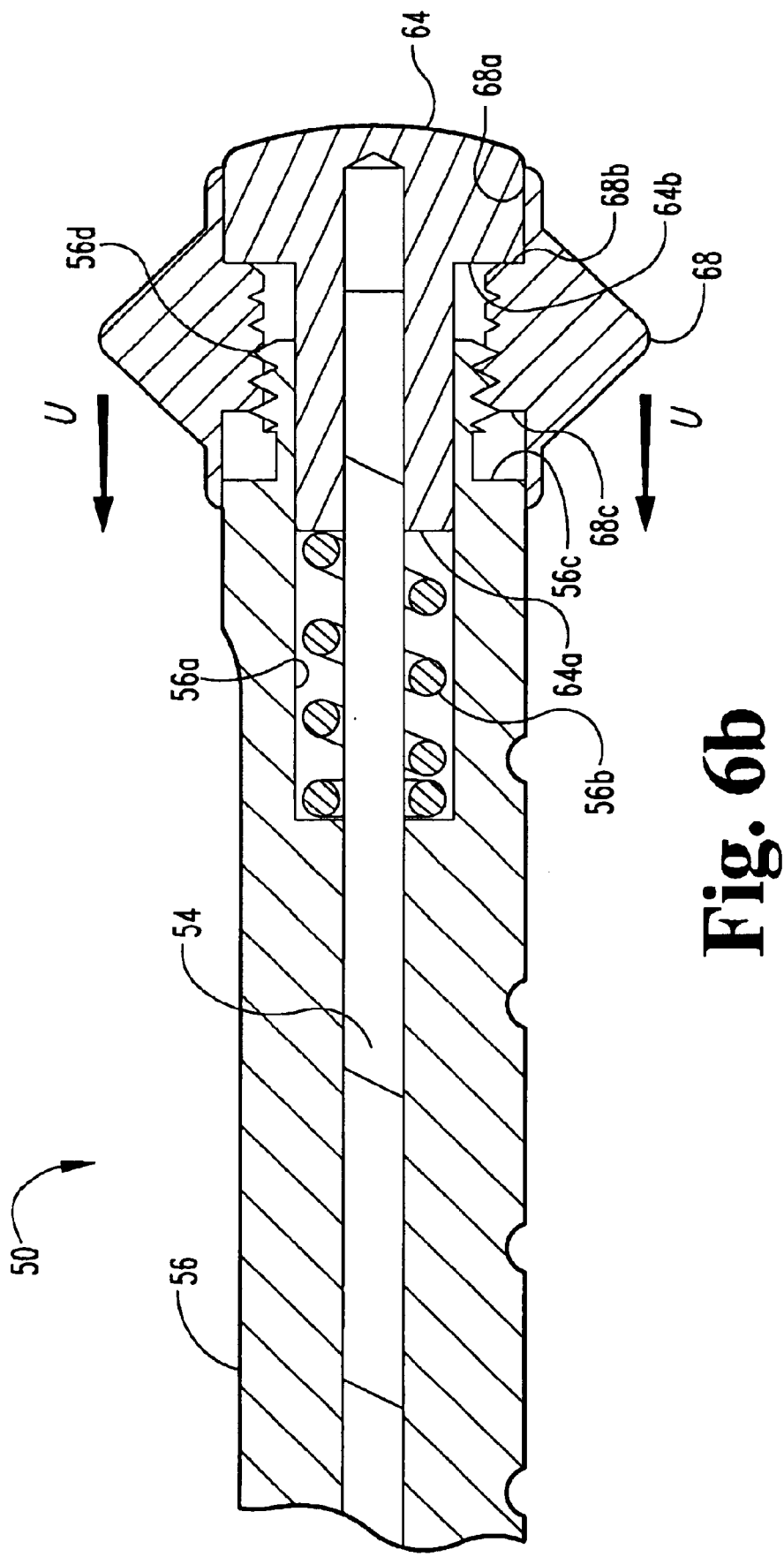
FIG. 6b is an enlarged cross-sectional view through the proximal end of the transfer instrument comprising a portion of the surgical instrument assembly of FIG. 1.

Referring now further to FIGS. 6a and 6b, transfer instrument 50 includes an outer sleeve 52 through which an inner shaft 54 extends. Outer sleeve 52 has a handle 56 along a proximal end thereof and a connector 58 at a distal end thereof. A locking member 68 is coupled to the proximal end of handle 56 and an actuator 64 is connected with inner shaft 54 at its proximal end.

Connector 58 has a hollow passage 59 opening at the distal end of connector 58. Passage 59 extends between a number of fingers 58a, 58b, 58c, and 58d and is in communication with a corresponding number of slots 59a, 59b, 59c and 59d located between respective ones of the number of fingers. Inner shaft 54 includes an enlarged cam member 66 at a distal end thereof positionable in passage 59. Connector 58 further includes a ball member 60 at a distal end thereof having a number of ball segments 60a, 60b, 60c, 60d formed by slots 59a, 59b, 59c, 59d. Each ball segment 60a, 60b, 60c, 60d includes a camming surface 61a, 61b, 61c, 61d, respectively, extending from a distal end of the respective ball segment to an inner contact surface 62a, 62b, 62c, and 62d.

Actuator 64 is in the form of a push button centered in locking member 68 at the proximal end of inner shaft 54. A spring 56b is positioned in a well 56a formed in handle 56 and in contact with a distal end 64a of actuator 64. Inner shaft 54 is spring-biased proximally with respect to outer sleeve 52 such that cam member 66 is normally positioned in or toward passage 59. Locking member 68 can be provided in the form of a wing nut or other threaded member that is threadingly engaged about a threaded stem 56d of handle 56.

In FIG. 6b locking member 68 is shown in a locked position with a proximal end surface 68b in contact with a ledge 64b of actuator 64, and with actuator 64 seated in a cavity 68a formed in locking member 68. To unlock transfer instrument 50, locking member 68 is threaded along stem 56d in the direction of arrows U until end surface 68c contacts ledge 56c of handle 56. When in the unlocked position, proximal end surface 68b of locking member 68 is spaced from actuator 64, and actuator 64 can be depressed to compress spring 56b and move cam member 66 distally beyond the distal end opening of passage 59. With cam member 66 extending beyond passage 59, fingers 58a, 58b, 58c, and 58d can collapse inwardly for positioning ball member 60 in or withdrawing it from transfer instrument receptacle 78. When actuator 64 is released, spring 56b biases cam member 66 at least partially into passage 59 at the distal ends of camming surfaces 61a, 61b, 61c, 61d. To lock insertion instrument 50, locking member 68 can be threaded in the direction opposite arrows U to the position shown in FIG. 6b. In the locked position, cam member 66 is pulled further into passage 59 and into contact with inner contact surface 62a, 62b, 62c, 62d to prevent ball member 60 from collapsing.

In order to couple transfer instrument 50 to operative element 70, locking member 68 is placed in its unlocked position so that actuator 64 can be depressed to push cam member 66 distally from passage 59. Ball member 60 is then collapsible for placement into receptacle 78. Actuator 64 is then released when ball member 60 is positioned in receptacle 78, and spring 56b withdraws cam member 66 at least partially into passage 59 toward camming surfaces 61a, 61b, 61c, 61d. In this position, the complementary spherical shapes of ball member 60 of connector 58 and instrument receptacle 78 allow transfer instrument 50 to pivot relative to operative element 70 yet remain engaged in receptacle 78 by upper lip 92.

To lock transfer member 50 and prevent it from pivoting relative to operative element 70, locking member 68 is threaded along stem 56d to its locked position, drawing cam member 66 along camming surfaces 61a, 61b, 61c, 61d and into contact with inner contact surface 62a, 62b, 62c, 62d, forcing ball segments 60a, 60b, 60c, 60d outwardly into frictional engagement with concave surface 96 of transfer instrument receptacle 78. Locking member 68 is threaded to its unlocked position so that transfer instrument 50 can be pivoted with respect to operative element 70 for repositioning, and then secured in this new position by threading lock member 68 to its locked position. When locking member 68 is in its unlocked position, actuator 64 can be depressed to allow ball member 60 to collapse as it is drawn past lip 92 of transfer instrument receptacle 78.

Figure 8:
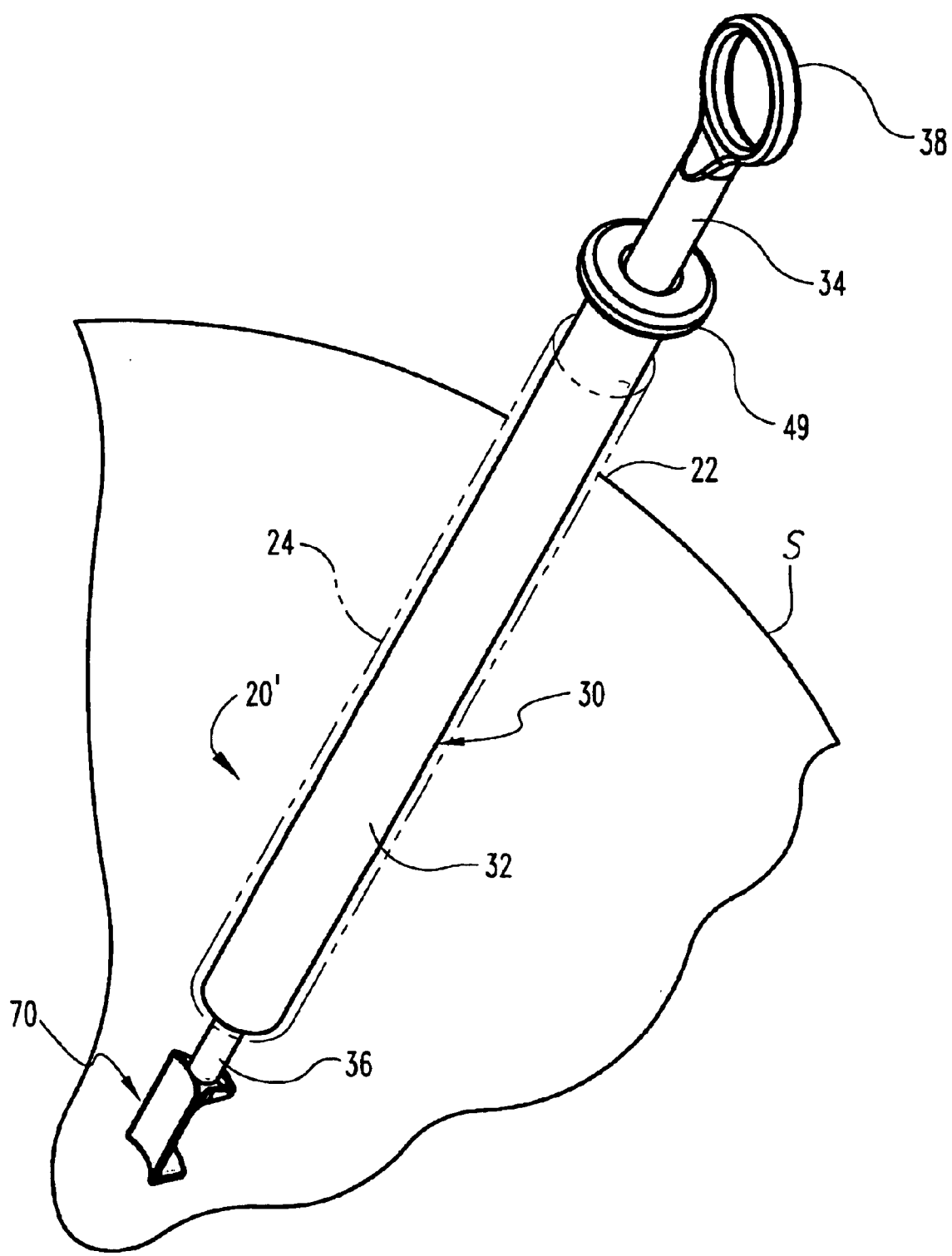
FIG. 8 illustrates the insertion instrument coupled to the operative element for positioning the operative element at an operative site into a patient's body through an access sleeve.
Figure 9:
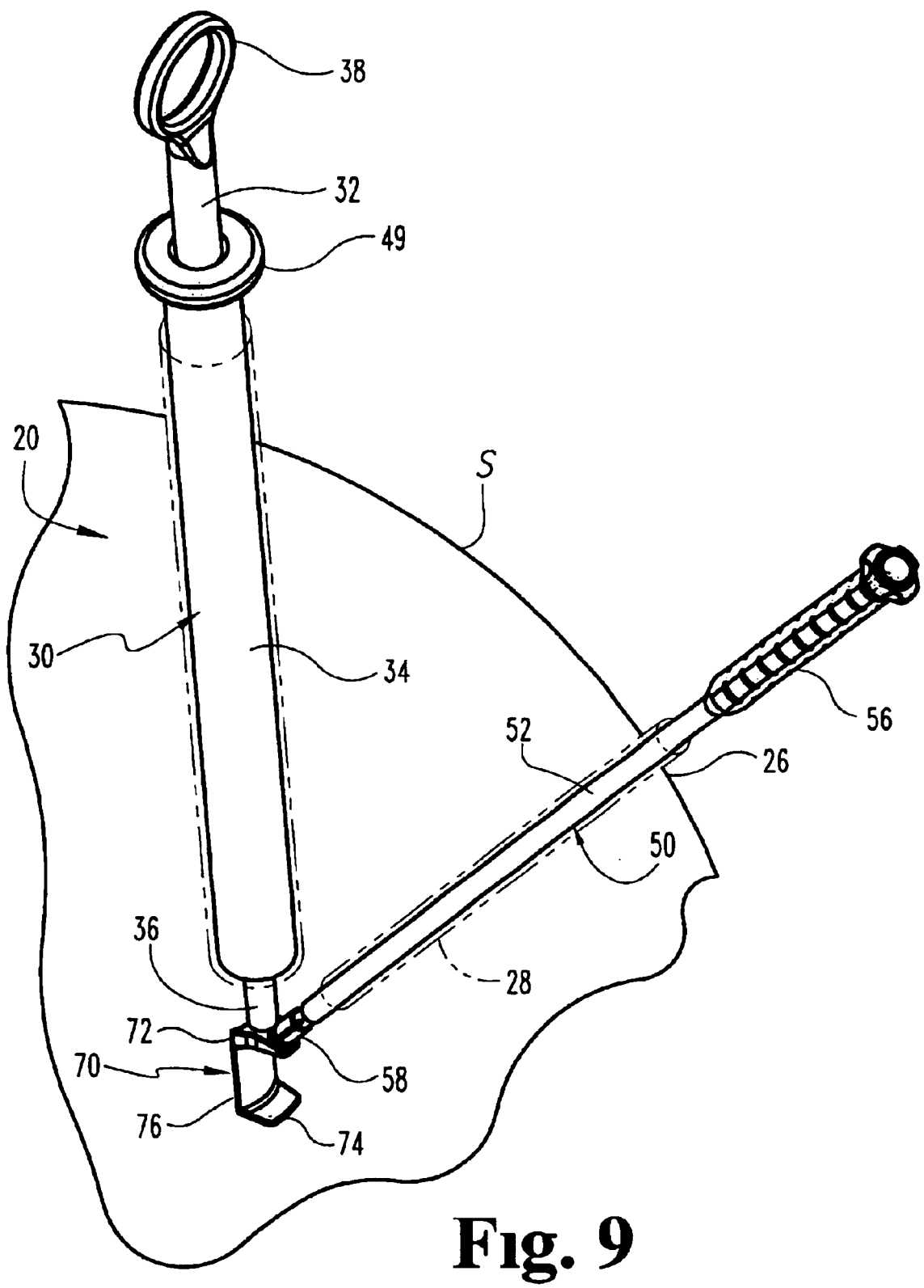
FIG. 9 illustrates the attachment of the transfer instrument to the operative element after the insertion instrument positions the operative element in the patient's body.
Figure 10:
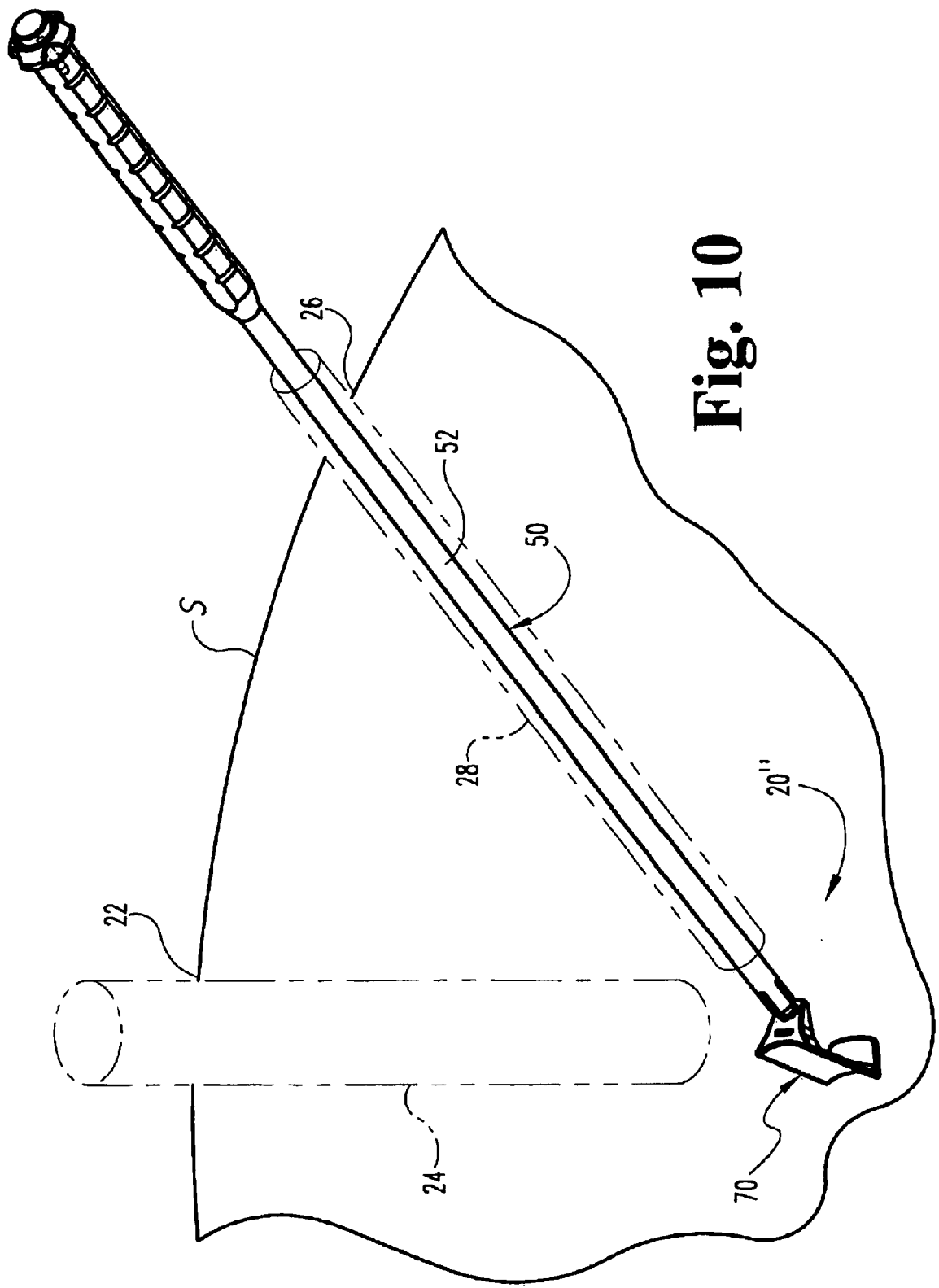
FIG. 10 illustrates the insertion instrument removed from the operative element with the transfer instrument coupled to the operative element in the patient's body.

Referring now to FIGS. 8–10, a method for using surgical instrument assembly 20 in a surgical procedure will be described. In FIG. 8 there is provided a first port 22 formed by an access sleeve 24 extending through skin S of the patient in an anterior approach to an operative site. It is contemplated that first port 22 can be formed using the instruments and techniques discussed in the publication by Sofamor Danek entitled *Surgical Technique Using Bone Dowel Instrumentation for Anterior Endoscopic Approach*. It is further contemplated that first port 22 can be formed by a laparoscopic housing on its proximal end that allows insertion of surgical instrument sub-assembly 20' through access sleeve 24 while the insufflated environment is maintained. Examples of such instruments are provided in the aforementioned publication by Sofamor Danek, in U.S. patent application Ser. No. 09/525,972, and in U.S. Pat. No. 6,228,022, each of which is incorporated herein by reference in its entirety. Non-laparoscopic approaches and instruments for forming first port 22 are also contemplated, such as those described in the Sofamor Danek publication entitled *Reduced Profile Instrumentation Surgical Technique*, the Sofamor Danek publication entitled *Anterior Instrumentation Surgical Technique*, and the Sofamor Danek publication entitled *Lumbar Tapered Fusion Device Surgical Technique*, each of which is incorporated herein by reference in their entirety. In another form, access sleeve 24 is a cannula to which an endoscope can be mounted or through which a microscope can aligned to visualize the operative site. Examples of microscopic and endoscopic systems are described in U.S. patent application Ser. No. 09/815,693, which is incorporated herein by reference in its entirety. First port 22 can also be a micro-incision through which the instruments of the present invention are directly positioned.

A surgical instrument sub-assembly 20' is provided that includes insertion instrument 30 coupled to operative element 70. Surgical instrument sub-assembly 20' is inserted through access sleeve 24 of first port 22 to the operative site in the patient. In FIG. 9, transfer instrument 50 extends through a second port 26 formed by access sleeve 28 positioned through the skin and tissue of the patient. Second port 26 can be formed in any manner as discussed above with respect to first port 22. Transfer instrument 50 is coupled to operative element 70 while insertion instrument 30 holds operative element 70 at the inserted location in the patient's body. In FIG. 10, insertion instrument 30 is removed to provide a second surgical instrument sub-assembly 20". Second surgical instrument sub-assembly 20" includes transfer instrument 50 coupled to operative element 70 to maintain it at the desired location relative to the operative site. Transfer instrument 50 can also be used to move or otherwise manipulate operative element 70 with respect to the operative site.

With insertion instrument 30 removed, access sleeve 24 is cleared for insertion of other instruments therethrough to the operative site. Operative element 70 can be withdrawn by reattaching insertion instrument 30 to second receptacle 80 and uncoupling transfer instrument 50 from first receptacle 78. Operative element 70 is then withdrawn with insertion instrument 30 through access sleeve 24, and transfer instrument 50 is withdrawn through access sleeve 28.

The present invention allows operative element 70 to be provided with a larger size than would be allowed if operative element 70 were inserted through second port 26. As such, the present invention allows the placement and use of larger operative elements at the surgical site. The present invention also allows the size of second port 26 to be minimized since the operative instruments can be inserted through a single large port 22 and handed off to a transfer instrument extending through the smaller port 26. In one specific example, access sleeve 24 provides an 18 millimeter diameter working channel and access sleeve 28 provides a 5 millimeter working channel. In this specific example, operative element 70 is a vein retractor 71 that fits through the 18 millimeter working channel, but is too large for insertion or withdrawal through the 5 millimeter working channel. It should be further understood that additional operative elements could be inserted through access sleeve 24 and handed-off or transferred to other transfer instruments extending through other ports defined by smaller diameter access sleeves.

Referring now to FIGS. 11–16, there are illustrated various surgical techniques employing an operative element 70 in the form of vein retractor 71 to retract the vasculature encountered and provide access to an operative site on the spinal column from an anterior approach. Proper retraction of the vasculature is critical for proper placement of spinal implants in the disc space in order to provide proper spacing and balanced bi-lateral support of the spinal column loads. In laparoscopic, endoscopic and other minimally invasive approaches to the operative site, the present invention enables the surgeon to properly retract the veins and arteries encountered to expose the operative site while protecting the vasculature from being damaged during the surgical procedure.

Surgical instrument sub-assembly 20" includes vein retractor 71 coupled to transfer instrument 50. Vein retractor 71 can be positioned at the operative site through access ports with an insertion instrument such as discussed above. Other surgical procedures for inserting surgical instrument sub-assembly 20" are also contemplated, including directly placing surgical instrument sub-assembly 20" through an open incision in which skin and tissue are retracted to expose the vasculature at the operative site.

With regard to the patient anatomy at the anterior, lower lumbar area of the spine, there is a main branch of the vena cava VC which bifurcates at about the L4–L5 vertebral level of the spinal column into left iliac vein LV and right iliac vein RV. There is further a main branch of the aorta A that bifurcates at about the L4–L5 vertebral level into left iliac artery LA and right iliac artery RA. Also shown are sacral artery SA and sacral vein SV which have been ligated. The vascular anatomy in the lumbar region can be classified based on the location of the aortic bifurcations and the left iliac vein LV relative to L4–L5 level. Further anatomical consideration for retracting vasculature to provide access to the operative site include the size of vasculature, scarring, atherosclerosis, and other anatomic variances. The present invention provides instruments and techniques for the surgeon to effectively handle these considerations in the vasculature anatomy.

Figure 12:
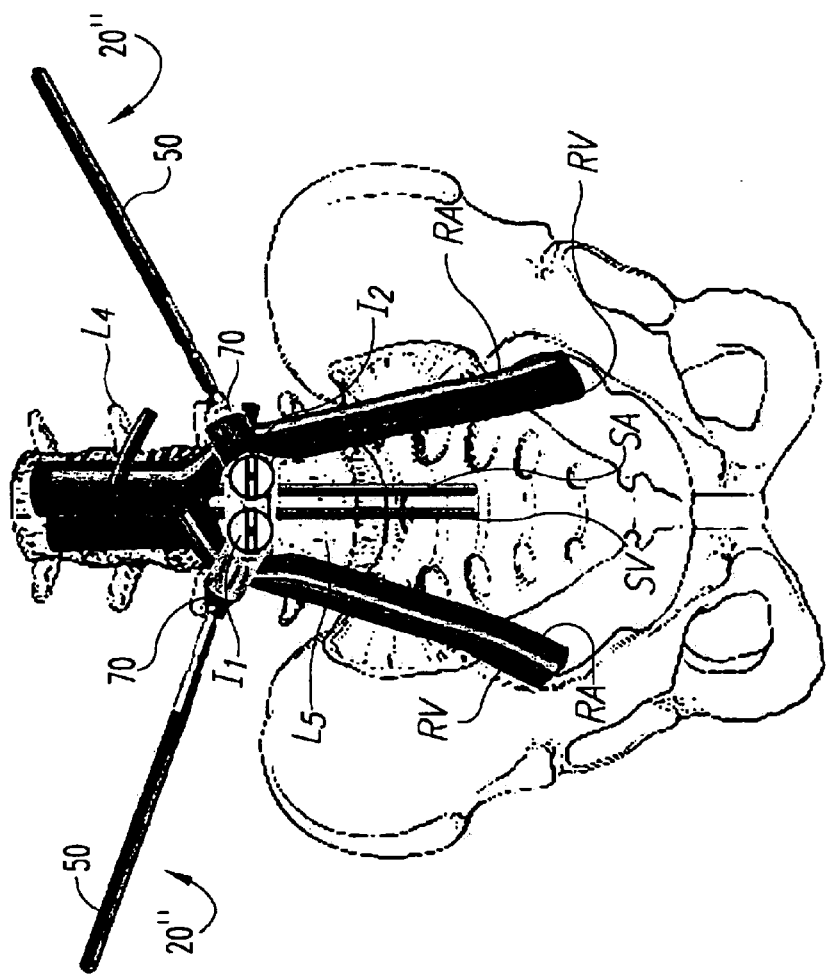
FIG. 12 illustrates a second vein retractor operative element along with the vein retractor of FIG. 11 used during the procedure at the operative site in the patient.
Figure 11:
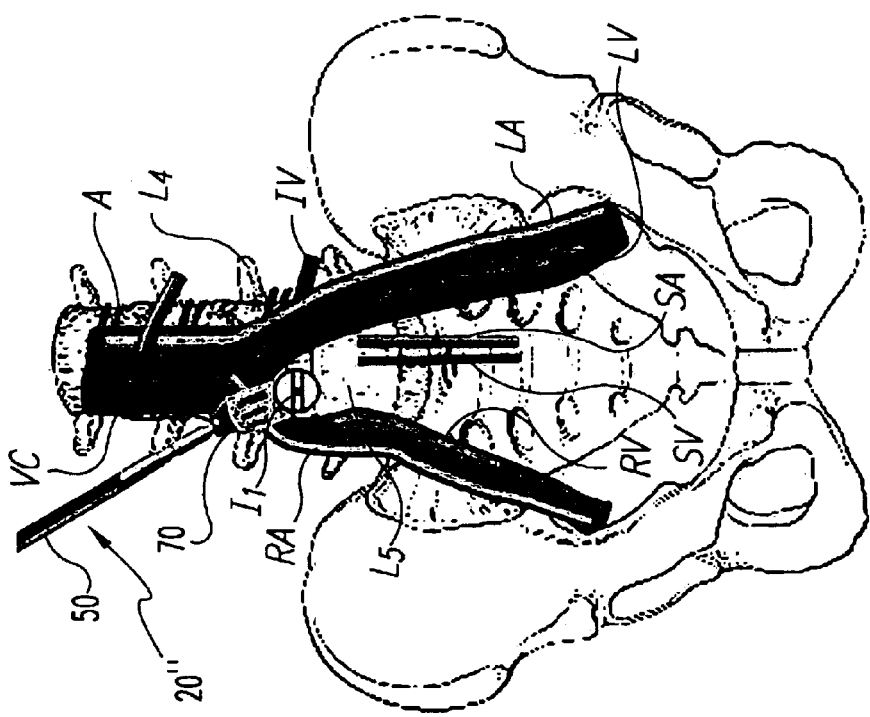
FIG. 11 illustrates one specific application for a vein retractor operative element for a procedure at an operative site in a patient.

FIGS. 11–12 illustrates a retraction technique for vascular anatomy that includes high bifurcation and high vein positioning relative to the L4–L5 vertebrae. Surgical instrument sub-assembly 20" includes vein retractor 71 positioned in the bifurcations of Vena Cava VC and aorta A to retract the right iliac artery RA and right iliac vein RV cephaladly and laterally to the right (relative to the patient) to expose a first bi-lateral location in the disc space between L4–L5 for insertion of implant I1 therein.

In FIG. 12 there is illustrated the use of another surgical instrument sub-assembly 20". Vein retractor 71 is positioned to retract the left iliac artery LA and left iliac vein LV cephaladly and laterally to the left (relative to the patient) to expose a second bi-lateral location in the disc space between L4–L5 for insertion of a second implant I2 therein. Implants I1 and I2 can be made from bone or other bio-compatible material, and can be provided in the form of a threaded implant, a push-in implant or fusion cage, or any other type of interbody device as would occur to those skilled in the art. It is further contemplated that the surgical instrument assembly of the present invention can be used to retract vasculature for attachment of a plate, rod, anchor or other device to the spinal column.

Figure 13:
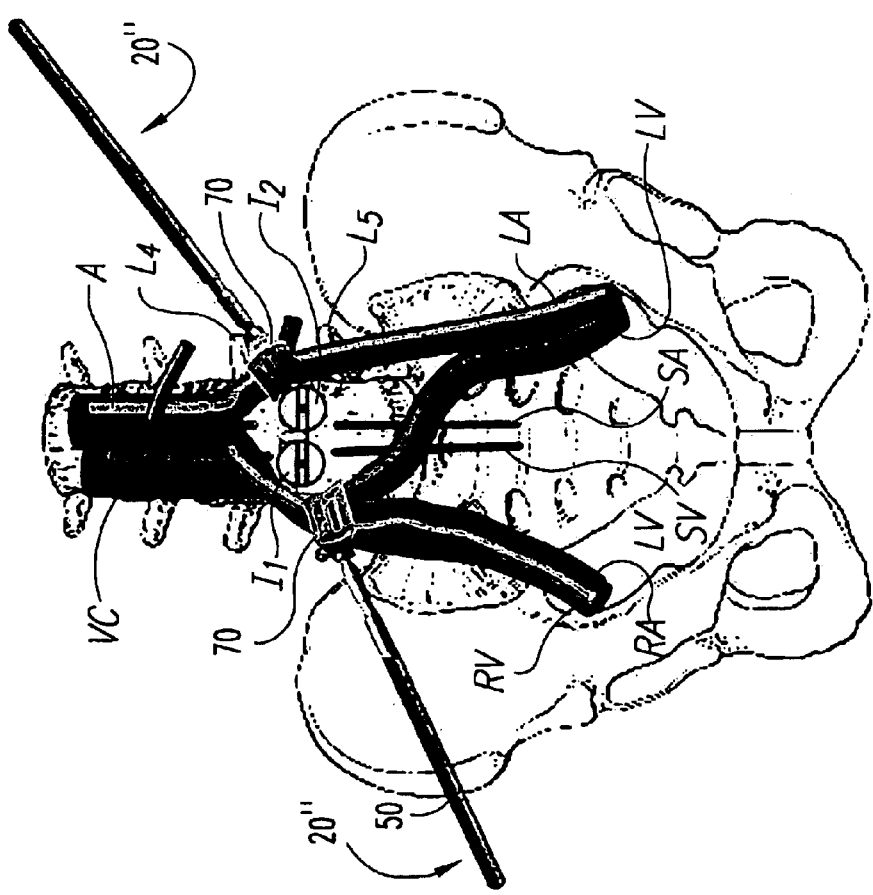
FIG. 13 illustrates a further specific application for two vein retractor operative elements used simultaneously for a procedure at an operative site in a patient.

FIG. 13 illustrates a retraction technique for vascular anatomy that includes high bifurcation and low vein positioning relative to the L4–L5 vertebrae. Vein retractor 71 is positioned to retract laterally to the right (relative to the patient) and slightly caudally right iliac vein RV, right iliac artery RA, and left iliac vein LV to expose a first bi-lateral disc space location on the right side of the disc space. Another surgical instrument sub-assembly 20" is positioned to retract laterally to the left and slightly cephaladly left iliac artery LA to expose a second bi-lateral disc space location of insertion of implant I2.

Figure 14:
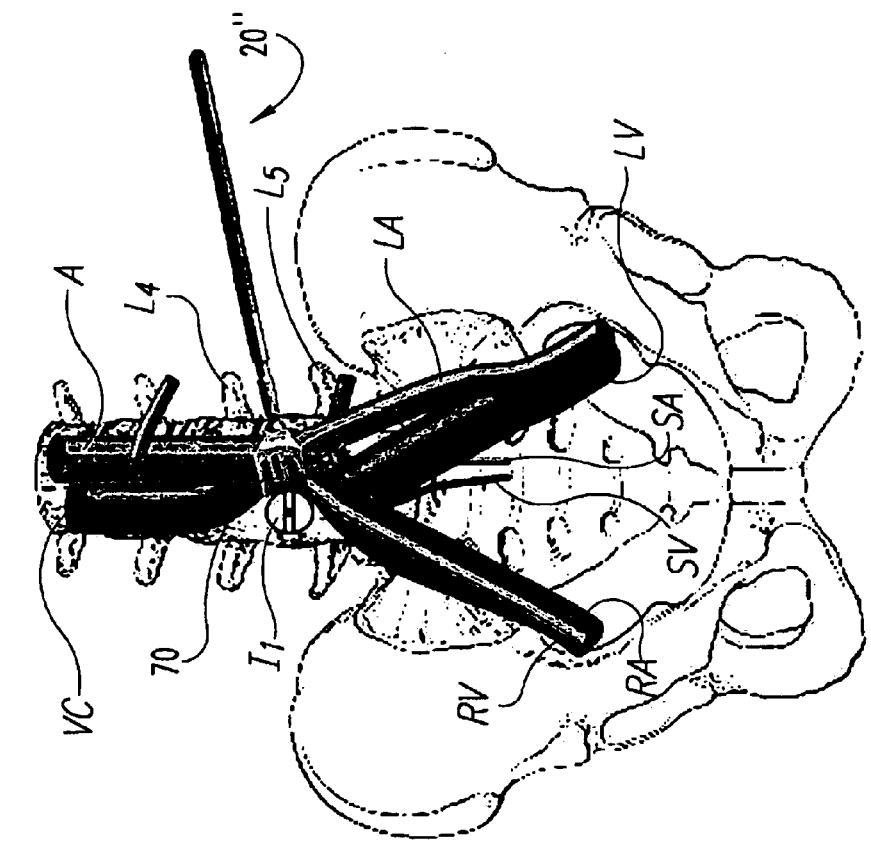
FIG. 14 illustrates still another specific application for a vein retractor operative element for a procedure at an operative site in a patient.
Figure 15:
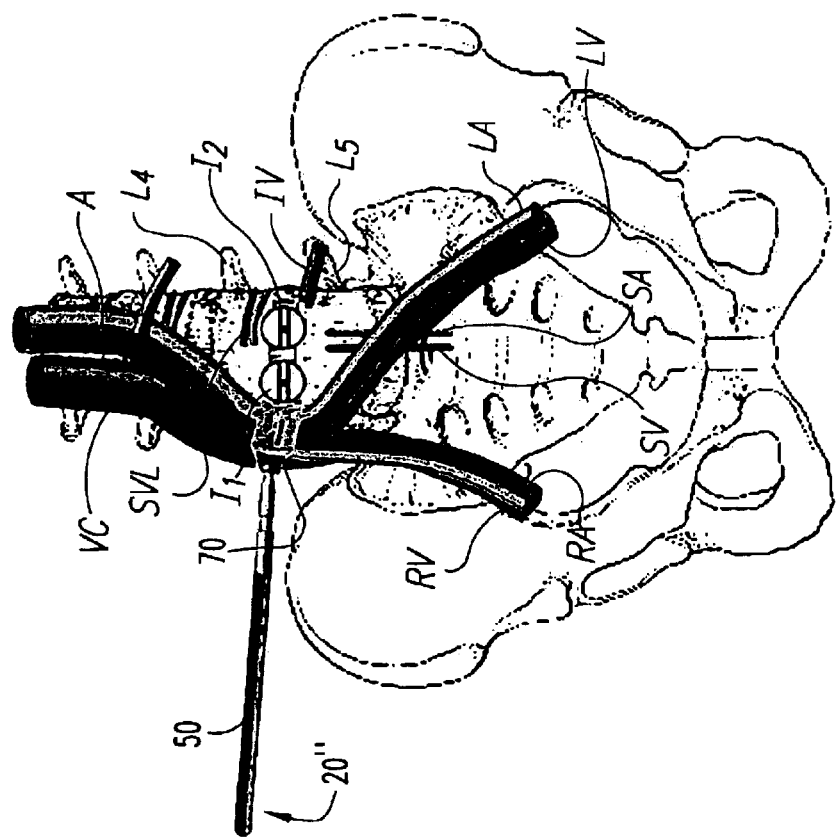
FIG. 15 illustrates a second vein retractor operative element used during the procedure of FIG. 14.

FIGS. 14–15 illustrate a retraction technique for vasculature anatomy having a low bifurcation and low vein positioning. In FIG. 14 surgical instrument sub-assembly 20" is positioned to retract laterally to the left (relative to the patient) the Vena Cava VC and aorta A to expose a first bi-lateral disc space location for insertion of implant I1. In FIG. 15, there is illustrated surgical instrument sub-assembly 20" positioned to retract laterally to the right (relative to the patient) the Vena Cava VC and aorta A to expose a second bi-lateral disc space location for insertion of implant I2. In this procedure ligation of the segment vessels SVL and iliolumbar vein IV along with sacral vessel SV and sacral artery SA facilitates retraction.

Figure 16:
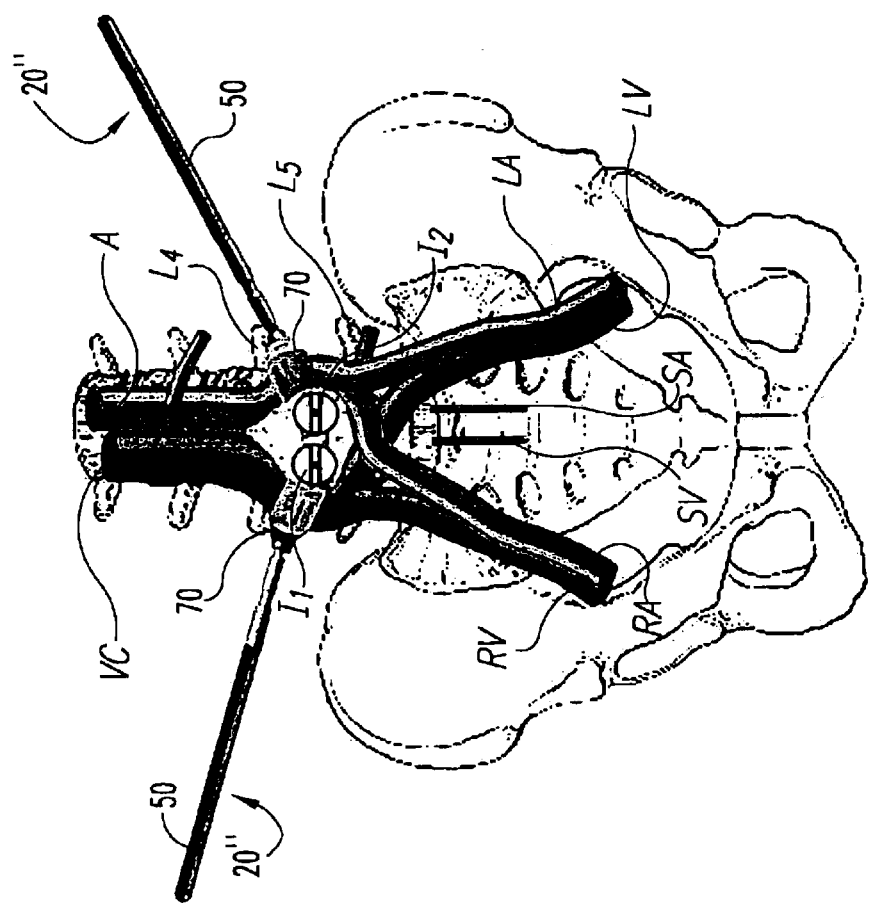
FIG. 16 illustrates another specific application for two vein retractor operative elements for a procedure at an operative site in a patient.

FIG. 16 illustrates an alternate retraction technique for vasculature anatomy having a low bifurcation and low vein positioning. A surgical instrument sub-assembly 20" is positioned to retract laterally to the right (relative to the patient) Vena Cava VC to expose a first bilateral disc space location. Another surgical instrument sub-assembly 20" is positioned to retract laterally to the left (relative to the patient) aorta A to expose a second bi-lateral disc space location. Implants I1 and I2 are inserted into the first and second bi-lateral disc space locations.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for retracting vasculature in the lumbar region of the spinal column via a minimally invasive anterior approach, the method comprising:

inserting a vein retractor to the lumbar region with an insertion instrument extending through a first port;

engaging the vein retractor with a transfer instrument extending through a second port;

disengaging and removing the insertion instrument; and positioning the vein retractor to retract the iliac artery and iliac vein of one of the left or right sides to expose a first bi-lateral location of a spinal disc space.

2. The method of claim 1, further comprising inserting a fusion implant in the spinal disc space at the first bi-lateral location.

3. The method of claim 2, further comprising:
  inserting a second vein retractor with an insertion instrument extending through the first port;
  engaging the vein retractor with a transfer instrument extending through a third port;
  disengaging and removing the insertion instrument; and
  positioning the vein retractor to retract the iliac artery and iliac vein of the other of the left or right sides to expose a second bi-lateral location of the spinal disc space.

4. The method of claim 3, further comprising inserting a second fusion implant in the spinal disc space at the second bi-lateral location.

5. The method of claim 3, wherein the first port is larger than the second port and the third port.

6. A method for retracting vasculature in the lumbar region of the spinal column via a minimally invasive anterior approach, the method comprising:
  inserting a first vein retractor to the lumber region with an insertion instrument extending through a first port;
  engaging the vein retractor with a transfer instrument extending through a second port;
  disengaging and removing the insertion instrument;
  positioning the first vein retractor to retract the left and right iliac veins and the right iliac artery toward the patient's right to expose a first bi-lateral location of a spinal disc space;
  inserting a second vein retractor to the lumbar region with an insertion instrument extending through the first port;
  engaging the vein retractor with a transfer instrument extending through a third port;
  disengaging and removing the insertion instrument; and
  positioning the second vein retractor to retract toward the patient's left the left iliac artery to expose a second bi-lateral location of the spinal disc space adjacent the first bi-lateral location.

7. The method of claim 6, further comprising inserting first and second fusion implants in the spinal disc space at corresponding ones of the first and second bi-lateral location.

8. A method for retracting vasculature in the lumbar region of the spinal column via a minimally invasive anterior approach, the method comprising:
  inserting a first vein retractor to the lumbar region with an insertion instrument extending through a first port;
  engaging the vein retractor with a first transfer instrument extending through a second port;
  disengaging and removing the insertion instrument;
  positioning the first vein retractor to retract the vena cava toward the patient's left to expose a first bi-lateral location of a spinal disc space;
  inserting a second vein retractor to the lumbar region with the insertion instrument extending through the first port;
  engaging the second vein retractor with a second transfer instrument extending through a third port;
  disengaging and removing the insertion instrument; and
  positioning the second vein retractor to retract the aorta towards the patient's right to expose a second bi-lateral location of the spinal disc space adjacent the first bi-lateral location.

9. The method of claim 8, further comprising inserting first and second fusion implants in the spinal disc space at corresponding ones of the first and second bi-lateral location.

10. A method for retracting vasculature in the lumbar region of the spinal column via a minimally invasive anterior approach, the method comprising:
  inserting a vein retractor to the lumber region with an insertion instrument extending through a first port;
  engaging the vein retractor with a transfer instrument extending through a second port;
  disengaging and removing the insertion instrument; and
  positioning the vein retractor to retract to one side of the patient the Vena Cava and aorta to expose a first bi-lateral location of a spinal disc space.

11. The method of claim 10, further comprising inserting a fusion implant in the spinal disc space at the first bi-lateral location.

12. The method of claim 11, further comprising:
  inserting a second vein retractor with an insertion instrument extending through the first port;
  engaging the second vein retractor with the transfer instrument extending through a third port;
  disengaging and removing the insertion instrument; and
  positioning the vein retractor to retract the Vena Cava and aorta to the other side of the patient to expose a second bi-lateral location of the spinal disc space.

13. The method of claim 12, further comprising inserting a second fusion implant in the spinal disc space at the second bi-lateral location.

14. A surgical instrument assembly, comprising:
  an operative element;
  an insertion instrument removably engaged to said operative element, said insertion instrument and said operative element being positionable in a patient to position said operative element at an operative site; and
  a transfer instrument positionable in the patient to engage said operative element at the operative site, wherein said operative element includes a first receptacle engageable by said transfer instrument and a second receptacle engageable by said insertion instrument, said first receptacle including a socket and said transfer instrument including a ball member at a distal end thereof pivotally engageable in said socket.

15. The surgical instrument assembly of claim 14, wherein:
  said transfer instrument includes a cam member disposed in a passage extending through said ball member; and
  said cam member is moveable in said passage with respect to said ball member from a first position wherein said cam member extends distally from said ball member whereby said ball member is collapsible for insertion into and removal from said socket to a second position wherein said cam member is positioned in said passage whereby said ball member is radially expanded to engage said socket.

16. The surgical instrument assembly of claim 15, wherein said transfer instrument includes a locking member for locking said cam member in said second position.

17. The surgical instrument assembly of claim 16, wherein said transfer instrument includes an actuator for moving said cam member to said first position when said locking member is unlocked.

18. A surgical instrument assembly, comprising:
  an operative element;
  an insertion instrument removably engaged to said operative element, said insertion instrument and said operative element being positionable in a patient to position said operative element at an operative site;

a transfer instrument positionable in the patient to engage said operative element at the operative site, wherein:
  said operative element includes a first receptacle engageable by said transfer instrument and a second receptacle engageable by said insertion instrument, said second receptacle including a first bore spaced from a second bore; and
  said insertion instrument including first and second engaging members having a slot extending therebetween, said first and second engaging members positionable in respective ones of said first and second bores to engage said insertion instrument to said operative element.

19. The surgical instrument assembly of claim 18, wherein said insertion instrument includes a locking member movable with respect to said first and second engaging members between a disengaged position whereby said first and second engaging members can be flexed toward one another for insertion into and removal from said first and second bores to an engaged position whereby said first and second engaging members are fixed with respect to one another to lock said first and second engaging members in said first and second bores.

20. A surgical instrument assembly, comprising:
  a vein retractor having a body extending between a first flange at one end of said body and a second flange at an another end of said body, said first flange having a first receptacle and a second receptacle;
  an insertion instrument removably engageable to said first receptacle of said vein retractor; and
  a transfer instrument removably engageable to said second receptacle of said vein retractor, wherein said transfer instrument is pivotally engageable to said vein retractor.

21. The surgical instrument assembly of claim 20, wherein:
  said insertion instrument and said vein retractor are engaged for positioning the vein retractor in a patient at an operative site; and
  said transfer instrument is engageable to said vein retractor after said vein retractor is positioned in the patient.

22. The surgical instrument assembly of claim 20, wherein said body has a concave surface along one side thereof extending between said first and second flanges and a convex surface on an opposite side extending between said first and second flanges.

23. The surgical instrument assembly of claim 20, wherein said first receptacle includes a socket and said transfer instrument includes a ball member at a distal end thereof engageable in said socket.

24. The surgical instrument assembly of claim 23, wherein:
  said transfer instrument includes a cam member disposed in a passage extending through said ball member; and
  said cam member is moveable in said passage with respect to said ball member from a first position wherein said cam member extends distally from said ball member whereby said ball member is collapsible for insertion into and removal from said socket to a second position wherein said cam member is positioned in said passage whereby said ball member is radially expanded to engage said socket.

25. The surgical instrument assembly of claim 20, wherein:
  said first receptacle includes a first bore spaced from a second bore; and
  said insertion instrument includes first and second engaging members including a slot extending therebetween, said first and second engaging members positionable in respective ones of said first and second bores to engage said insertion instrument to said operative element.

26. The surgical instrument assembly of claim 25, wherein said insertion instrument includes a locking member movable with respect to said first and second engaging members between a disengaged position whereby said first and second engaging members can be flexed toward one another for insertion into and removal from said first and second bores to an engaged position whereby said first and second engaging members are fixed with respect to one another to lock said first and second engaging members in said first and second bores.

27. A surgical instrument assembly, comprising:
  a vein retractor having a body extending between a first flange at one end of said body and a second flange at an another end of said body, said first flange having a first receptacle and a second receptacle;
  an insertion instrument removably engageable to said first receptacle of said vein retractor; and
  a transfer instrument removably engageable to said second receptacle of said vein retractor, wherein said second receptacle includes a socket and said transfer instrument includes a ball member at a distal end thereof engageable in said socket.

28. The surgical instrument assembly of claim 27, wherein:
  said transfer instrument includes a cam member disposed in a passage extending through said ball member; and
  said cam member is moveable in said passage with respect to said ball member from a first position wherein said cam member extends distally from said ball member whereby said ball member is collapsible for insertion into and removal from said socket to a second position wherein said cam member is positioned in said passage whereby said ball member is radially expanded to engage said socket.

29. The surgical instrument assembly of claim 27, wherein:
  said first receptacle includes a first bore spaced from a second bore; and
  said insertion instrument includes first and second engaging members including a slot extending therebetween, said first and second engaging members positionable in respective ones of said first and second bores to engage said insertion instrument to said operative element.

30. The surgical instrument assembly of claim 28, wherein said insertion instrument includes a locking member movable with respect to said first and second engaging members between a disengaged position whereby said first and second engaging members can be flexed toward one another for insertion into and removal from said first and second bores to an engaged position whereby said first and second engaging members are fixed with respect to one another to lock said first and second engaging members in said first and second bores.

31. A surgical instrument assembly, comprising:
  an operative element;
  an insertion instrument removably engaged to said operative element, said insertion instrument and said operative element being positionable in a patient to position said operative element at an operative site; and
  a transfer instrument positionable in the patient to engage said operative element at the operative site, wherein said transfer instrument is pivotal relative to said operative element for repositioning relative thereto.

32. The surgical instrument assembly of claim 31, wherein said transfer instrument is lockable with said operative element to fix a position relative thereto.

33. The surgical instrument assembly of claim 31, wherein said operative element is a vein retractor.

34. The surgical instrument assembly of claim 33, wherein said vein retractor includes a body having a first flange extending from one end of said body and a second flange extending from an opposite end of said body.

35. The surgical instrument assembly of claim 34, wherein said body has a concave surface along one side thereof extending between said first and second flanges and a convex surface on an opposite side extending between said first and second flanges.

36. The surgical instrument assembly of claim 31, wherein said operative element includes a first receptacle engageable by said transfer instrument and a second receptacle engageable by said insertion instrument.

37. The surgical instrument assembly of claim 36, wherein said first receptacle includes a socket and said transfer instrument includes a ball member at a distal end thereof pivotally engageable in said socket.

38. The surgical instrument assembly of claim 37, wherein:
said member includes a cam member disposed in a passage extending through said ball member; and
said cam member is moveable in said passage with respect to said ball member from a first position wherein said cam member extends distally from said ball member whereby said ball member is collapsible for insertion into and removal from said socket to a second position wherein said cam member is positioned in said passage whereby said ball member is radially expanded to engage said socket.

39. The surgical instrument assembly of claim 38, wherein said member includes a locking member for locking said cam member in said second position.

40. The surgical instrument assembly of claim 36, wherein:
said second receptacle includes a first bore spaced from a second bore; and
said insertion instrument includes first and second engaging members having a slot extending therebetween, said first and second engaging members positionable in respective ones of said first and second bores to engage said insertion instrument to said operative element.

41. The surgical instrument assembly of claim 40, wherein said insertion instrument includes a locking member movable with respect to said first and second engaging members between a disengaged position whereby said first and second engaging members can be flexed toward one another for insertion into and removal from said first and second bores to an engaged position whereby said first and second engaging members are fixed with respect to one another to lock said first and second engaging members in said first and second bores.

42. A surgical instrument assembly, comprising:
an operative element comprising a vein retractor, wherein said vein retractor includes a body comprising a first flange extending from one end of said body and a second flange extending from an opposite end of said body, wherein said body further includes a concave surface along one side thereof extending between said first and second flanges and a convex surface on an opposite side extending between said first and second flanges;
an insertion instrument removably engaged to said operative element, said insertion instrument and said operative element being positionable in a patient to position said operative element at an operative site; and
a transfer instrument positionable in the patient to engage said operative element at the operative site, wherein said transfer instrument is pivotal with respect to said operative element when engaged thereto.

43. The surgical instrument assembly of claim 42, wherein said insertion instrument and said operative element are inserted through a first port in the patient to position said operative element at the operative site and said transfer instrument is inserted through a second port when positioned in the patient to engage the operative element at the operative site.

44. A method for positioning an operative element at an operative site in a patient, comprising:
inserting the operative element through a first port in the patient with an insertion instrument;
inserting a transfer instrument through a second port in the patient; and
engaging the operative element with the transfer instrument; and
repositioning the transfer instrument relative to the operative element while maintaining engagement therewith, wherein repositioning the transfer instrument includes pivoting the transfer instrument relative to the operative element.

45. The method of claim 44, further comprising locking the transfer instrument with the operative element to prevent movement therebetween.

46. The method of claim 44, further comprising removing the insertion instrument.

47. The method of claim 44, wherein the first port is formed by an access sleeve.

48. The method of claim 44, wherein the first port is larger than the second port and the operative element has a size preventing it from passing through the second port.

49. The method of claim 44, wherein the first and second ports provide an anterior approach to the operative site.

50. A surgical instrument assembly, comprising:
an operative element;
an insertion instrument removably engaged to said operative element, said insertion instrument and said operative element being positionable in a patient to position said operative element at an operative site; and
a transfer instrument positionable in the patient to engage said operative element at the operative site, said transfer instrument including a member movable from a first position wherein said transfer instrument is movably engaged with said operative element to a second position wherein said transfer instrument is fixedly engaged with said operative element, wherein said transfer instrument is pivotal with respect to said operative element when movably engaged thereto.

51. The surgical instrument assembly of claim 50, wherein said insertion instrument and said operative element are inserted through a first port in the patient to position said operative element at the operative site and said transfer instrument is inserted through a second port when positioned in the patient to engage the operative element at the operative site.

52. The surgical instrument assembly of claim 50, wherein said operative element is a vein retractor.

53. The surgical instrument assembly of claim 52, wherein said vein retractor includes a body having a first flange extending from one end of said body and a second flange extending from an opposite end of said body.

54. The surgical instrument assembly of claim 53, wherein said body has a concave surface along one side thereof extending between said first and second flanges and a convex surface on an opposite side extending between said first and second flanges.

55. The surgical instrument assembly of claim 50, wherein said operative element includes a first receptacle engageable by said transfer instrument and a second receptacle engageable by said insertion instrument.

56. The surgical instrument assembly of claim 55, wherein said first receptacle includes a socket and said transfer instrument includes a ball member at a distal end thereof pivotally engageable in said socket.

57. The surgical instrument assembly of claim 56, wherein:
   said member includes a cam member disposed in a passage extending through said ball member; and
   said cam member is moveable in said passage with respect to said ball member from a first position wherein said cam member extends distally from said ball member whereby said ball member is collapsible for insertion into and removal from said socket to a second position wherein said cam member is positioned in said passage whereby said ball member is radially expanded to engage said socket.

58. The surgical instrument assembly of claim 57, wherein said member includes a locking member for locking said cam member in said second position.

59. The surgical instrument assembly of claim 55, wherein:
   said second receptacle includes a first bore spaced from a second bore; and
   said insertion instrument includes first and second engaging members having a slot extending therebetween, said first and second engaging members positionable in respective ones of said first and second bores to engage said insertion instrument to said operative element.

60. The surgical instrument assembly of claim 59, wherein said insertion instrument includes a locking member movable with respect to said first and second engaging members between a disengaged position whereby said first and second engaging members can be flexed toward one another for insertion into and removal from said first and second bores to an engaged position whereby said first and second engaging members are fixed with respect to one another to lock said first and second engaging members in said first and second bores.

* * * * *

UNITED STATES PATENT AND TRADEMARK OFFICE
CERTIFICATE OF CORRECTION

PATENT NO. : 6,723,043 B2
DATED : April 20, 2004
INVENTOR(S) : Thomas J. Kleeman and James P. Duncan It is certified that error appears in the above-identified patent and that said Letters Patent is hereby corrected as shown below:

<u>Column 12,</u>
Line 49, please delete "28" and insert -- 29 --.

Signed and Sealed this

Twenty-eighth Day of September, 2004

JON W. DUDAS
*Director of the United States Patent and Trademark Office*